United States Patent
Hoekstra et al.

(12)

(10) Patent No.: US 6,303,625 B1
(45) Date of Patent: Oct. 16, 2001

(54) TRIAZOLOPYRIDINES FOR THE TREATMENT OF THROMBOSIS DISORDERS

(75) Inventors: William J. Hoekstra, Villanova; Edward C. Lawson, Lansdale; Bruce E. Maryanoff, Forest Grove, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/354,032

(22) Filed: Jul. 15, 1999

Related U.S. Application Data

(60) Provisional application No. 60/094,231, filed on Jul. 27, 1998.

(51) Int. Cl.[7] .................. A61K 31/437; A61K 31/4545; C07D 471/04; C07D 401/14; C07D 403/14; A61P 7/02

(52) U.S. Cl. .............. 514/303; 514/212.06; 514/253.04; 514/383; 540/518; 544/362; 544/366; 546/120; 548/262.4

(58) Field of Search .................. 546/120; 514/303, 514/212.06, 253.04, 383; 540/518; 544/362, 366; 548/262.4

(56) References Cited

U.S. PATENT DOCUMENTS

| | | | |
|---|---|---|---|
| 3,050,525 | 8/1962 | Bicking | 260/296 |
| 6,043,369 | * 3/2000 | Schefczik | 546/119 |

FOREIGN PATENT DOCUMENTS

| | | |
|---|---|---|
| 0 655 439 A2 | 5/1995 | (EP) . |
| WO 94/18981 | 9/1994 | (WO) . |

OTHER PUBLICATIONS

Frolund B et al. J. Med. Chem. 38(17), 3287–96, 1995.*
Zablocki, J. A., et al., "Fibrinogen Receptor Antagonists", Current Pharmaceutical Design, 1995 1. 533–558.
Alig, L., et al., "Low Molecular Weight, Non–Peptide Fibrinogen Receptor Antagonists", J. Med. Chem. 1992, 35, 4393–4407.
Cox, D., et al., "Targets in Integrin Research", Drugs News & Perspectives, May 1995.
Krakowiak, K. "New Synthesis of Per–N–Alkyl–subsstituted Triaza–and Tetraaza–Crown Compounds Containing an Allyloxymethyl Substituent", J. Heterocyclic Chem., May–Jun. 1989, 661–665.
Rico, J. et al., "A Highly Stereoselective Michael Addition to an ,β–Unsaturated Ester as the Crucial Step in the Synthesis of a Novel β–Amino Acid–Containing Fibrinogen Receptor Antagonist", J. Org. Chem., 1993 58, 7948–7951.
Jeffrey, T "Cooper (I) and Phase Transfer Catalysed Allylic Substitution by Terinal Alkynes", Tetrahedron Letters, vol. 30, No. 17, 2225–2228, 1989.
Shearer, Barry G. "S–2–Naphthylmethyl Thiocetimidate Hydrobromide: A New Odorless Reagents for the Mild Synthesis of Substituted Acetamidines", Tetrahedron Letters, vol. 38, No. 2, 1997, 179–182.

* cited by examiner

*Primary Examiner*—Evelyn Mei Huang
(74) *Attorney, Agent, or Firm*—Hal Woodrow

(57) ABSTRACT

The invention is directed to novel triazolopyridine derivatives which are useful as antagonists of GPIIb/IIIa. Pharmaceutical compositions comprising the triazolopyridine derivatives of the present invention, methods of treating conditions mediated by GPIIb/IIIa (e.g., methods for treating platelet-mediated thrombotic disorders) along with processes for making the compounds and novel intermediates are also disclosed.

23 Claims, No Drawings

TRIAZOLOPYRIDINES FOR THE TREATMENT OF THROMBOSIS DISORDERS

CROSS-REFERENCE TO RELATED APPLICATION

This application claims priority from U.S. provisional application Ser. No. 60/094,231, filed Jul. 27, 1998, the contents of which are hereby incorporated by reference.

FIELD OF THE INVENTION

This invention relates to certain novel compounds, their synthesis and their use for the treatment of thrombosis disorders. More particularly, the compounds are fibrinogen receptor antagonists which inhibit platelet aggregation and are useful in treating thrombotic disorders.

BACKGROUND OF THE INVENTION

Platelet aggregation constitutes the initial hemostatic response to curtail bleeding induced by vascular injury. However, pathological extension of this normal hemostatic process can lead to thrombus formation. The final, common pathway in platelet aggregation is the binding of fibrinogen to activated, exposed platelet glycoprotein IIb/IIIa (GPIIb/IIIa). Agents which interrupt binding of fibrinogen to GPIIb/IIIa, therefore, inhibit platelet aggregation. These agents are, therefore, useful in treating platelet-mediated thrombotic disorders such as arterial and venous thrombosis, acute myocardial infarction, unstable angina, re-occlusion following thrombolytic therapy and angioplasty, inflammation, and a variety of vaso-occlusive disorders. The fibrinogen receptor (GPIIb/IIIa) is activated by stimuli such as ADP, collagen, and thrombin exposing binding domains to two different peptide regions of fibrinogen: alpha-chain Arg-Gly-Asp (RGD) and gamma-chain His-His-Leu-Gly-Gly-Ala-Lys-Gln-Ala-Gly-Asp-Val (HHLGGAKQAGDV, γ400–411). Since these peptide fragments themselves have been shown to inhibit fibrinogen binding to GPIIb/IIIa, a mimetic of these fragments would also serve as an antagonist. In fact, prior to this invention, potent RGDbased antagonists have been revealed which inhibit both fibrinogen binding to GPIIb/IIIa and platelet aggregation e.g., Ro-438857 (L. Alig, *J. Med. Chem.* 1992, 35, 4393) has an $IC_{50}$ of 0.094 $\mu$M against in vitro thrombin-induced platelet aggregation. Some of these agents have also shown in vivo efficacy as antithrombotic agents and, in some cases, have been used in conjunction with fibrinolytic therapy e.g., t-PA or streptokinase, as well (J. A. Zablocki, *Current Pharmaceutical Design* 1995, 1, 533).

Accordingly, it is an object of the invention to identify compounds which are antagonists of GPIIb/IIIa. It is another object of the invention to identify compounds which inhibit platelet aggregation by inhibiting the binding of fibrinogen to GPIIb/IIIa. Another object of this invention is to identify compounds which are useful for treating thrombotic disorders. Still another object of the invention is to identify methods for treating thrombosis disorders using the compounds of the present invention.

We now describe a series of triazolopyridine compounds which act as antagonists of GPIIb/IIIa and are useful for treating thrombotic disorders.

SUMMARY OF THE INVENTION

The present invention is directed to compounds represented by the following general formula (I) or (II):

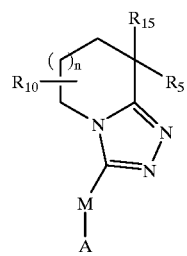

(I)

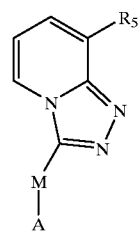

(II)

wherein M is $(CH_2)_m$, CH=CH, CH=CF, CF=CH, or C≡C;

n is can integer selected from 0, 1 or 2;

A is selected from piperidin-2-yl, piperidin-3-yl, piperidin-4-yl, piperazin-1-yl, pyrrolidin-2-yl, pyrrolidin-3-yl, $NHR_2$ or

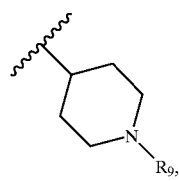

wherein $R_9$ is selected from hydrogen, $C_1$-$C_8$ alkyl, CH=(NH), CMe=(NH), $C_2$-$C_6$ acyl, $C_1$-$C_8$ alkoxycarbonyl or ar($C_1$-$C_8$ alkoxy)carbonyl, preferably, $R_9$ is hydrogen;

$R_2$ is selected from hydrogen, $C_1$-$C_8$ alkyl or $C_2$-$C_6$ acyl, preferably, $R_2$ is hydrogen;

$R_{10}$ is selected from hydrogen or $C(O)N(R_1)YZ$, wherein $R_1$ is selected from hydrogen, $C_1$-$C_8$ alkyl or $C_3$-$C_8$ cycloalkyl, preferably $R_{10}$ is hydrogen;

Y is selected from $(CH_2)_p$, $CH(R_3)(CH_2)_q$, $(CH_2)_qCH(R_3)$, $(CH(CO_2R_4)CH_2)_q$, $(CH_2)_qCHOH$ or piperidine-3-carboxylic acid;

$R_3$ is selected from $C_1$-$C_8$ alkyl, $C_2$-$C_8$ alkenyl, $C_2$-$C_8$ alkynyl, aryl, ar($C_1$-$C_8$)alkyl or heteroaryl;

$R_4$ is selected from hydrogen, $C_1$-$C_8$ alkyl or $C_3$-$C_8$ cycloalkyl, preferably, is hydrogen;

p is an integer selected from 2 or 3;

q is an integer selected from 1, 2, or 3, preferably, q is 1;

Z is $CO_2R_8$;

$R_5$ is selected from hydrogen or $C(O)NHQ(CHW)_rCO_2R_8$, preferably $R_5$ is $C(O)NHQ(CHW)_rCO_2R_8$;

wherein Q is selected from $CH_2$, CH-aryl, CH-heteroaryl, CH-substituted-heteroaryl or CH-($C_1$-$C_8$)alkyl, preferably, Q is $CH_2$, CH-substituted-heteroaryl or CH-heteroaryl;

W is selected from hydrogen or $N(R_6)T$-$R_7$, preferably W is hydrogen when Q is CH-aryl or CH-heteroaryl, and W is $N(R_6)T$-$R_7$ when Q is $CH_2$;

R₆ is selected from hydrogen, C₁–C₈ alkyl or C₂–C₆ acyl, preferably, R₆ is hydrogen;

T is selected from C(O), C(N—CN) or SO₂, preferably, T is C(O);

R₇ is selected from C₁–C₈ alkyl, aryl, ar(C₁–C₈)alkyl, ar(C₁–C₈)alkoxy, C₁–C₈ alkoxy, (C₁–C₈)alkylamino or unsubstituted or substituted heteroaryl(C₀–C₈)alkyl; and R₈ is hydrogen, C₁–C₈ alkyl, or CH₂C(O)NR₁₁R₁₂, preferably, R₈ is hydrogen or CH₂C(O)NR₁₁R₁₂; wherein R₁₁ and R₁₂ are each independently selected from hydrogen, C₁–C₈ alkyl, or C₃–C₈ cycloalkyl, preferably, R₁₁ and R₁₂ are C₁–C₈ alkyl;

m is an integer selected from 1, 2, or 3, preferably, m is 1 or 2;

r is an integer selected from 0 or 1; and

R₁₅ is selected from hydrogen or C₁–C₈ alkyl preferably, R₁₅ is hydrogen; and pharmaceutically acceptable salts thereof.

Preferably, the compounds of the present invention are of the formula

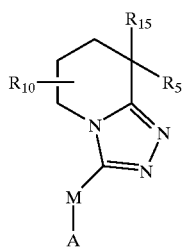

(I)

wherein M is (CH₂)ₘ, CH=CH, or C≡C; and all other variables are as defined above; and pharmaceutically acceptable salts thereof.

In one embodiment of the invention is the compound of formula (I) or (II), wherein:

wherein M is (CH₂)ₘ or CH=CH;

R₅ is C(O)NHQ(CHW)ᵣCO₂R₈;

wherein Q is selected from CH₂, CH-heteroaryl or CH-substituted-heteroaryl;

W is selected from hydrogen or N(R₆)T-R₇;

wherein R₆ is H; T is C(O);

R₇ is selected from C₁–C₈ alkyl, aryl, ar(C₁–C₈)alkyl, ar(C₁–C₈)alkoxy, C₁–C₈ alkoxy, or (C₁–C₈) alkylamino;

R₈ is hydrogen, C₁–C₈ alkyl or CH₂C(O)NR₁₁R₁₂; wherein R₁₁ and R₁₂ are each independently C₁–C₈ alkyl;

R₁₀ is hydrogen;

R₁₅ is selected from hydrogen or C₁–C₄ alkyl;

r is 1;

and all other variables are as defined above;

and pharmaceutically acceptable salts thereof.

In a class of the invention is the compound of formula (I) selected from:

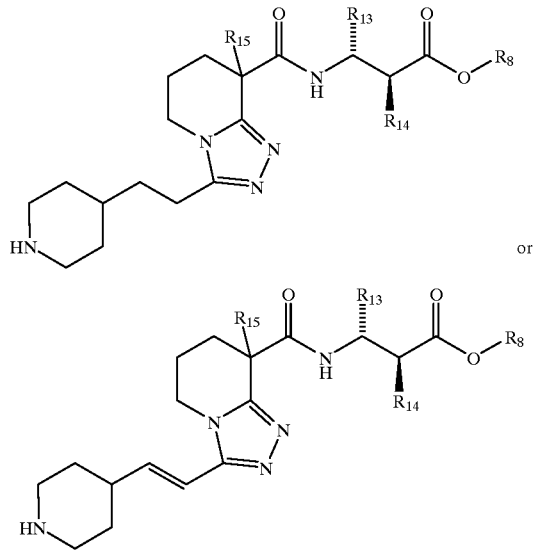

wherein R₈ is hydrogen or CH₂CONEt₂;
R₁₃ is selected from hydrogen, 3-pyridyl or 3-quinolinyl;
R₁₄ is selected from hydrogen or NHCO₂CH₂Ph; and
R₁₅ is selected from hydrogen or methyl;
and pharmaceutically acceptable salts thereof.

Exemplifying the invention is the compound of formula (I) selected from:

β-[[[5,6,7,8-Tetrahydro-3-[2-(4-piperidinyl)ethyl]-1,2,4-triazolo[4,3-a]pyridin-8-yl]carbonyl]amino]-βS-3-pyridinepropanoic acid;

β-[[[5,6,7,8-Tetrahydro-3-[2-(4-piperidinyl)ethyl]-1,2,4-triazolo[4,3-a]pyridin-8-yl]carbonyl]amino]-β-propanoic acid;

β-[[[5,6,7,8-Tetrahydro-3-[2-(4piperidinyl)ethyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)ethyl]-1,2,4-triazolo[4,3-a]pyridin-8-yl]carbonyl]amino]-βS-3-pyridinepropanoic acid 2-(Diethylamino)-2-oxoethyl ester;

β-[[[5,6,7,8-Tetrahydro-3-[2-(4-piperidinyl)ethenyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)ethyl]-1,2,4-triazolo[4,3-a]pyridin-8-yl]carbonyl]amino]-αS-benzyloxycarbonylamino-propanoic acid 2-(Diethylamino)-2-oxoethyl ester;

β-[[[5,6,7,8-Tetrahydro-3-[2-(4-piperidinyl)ethyl]-1,2,4-triazolo[4,3-a]pyridin-8-yl]carbonyl]amino]-β-3-thiophenepropanoic acid; or β-[[[5,6,7,8-Tetrahydro-8-methyl-3-[2-(4-piperidinyl)ethyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)Z-1-fluoroethenyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-β-4-pyridinepropanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-4-(3,5-dimethylisoxazolyl)sulfonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-βS-3-pyridylpropanoic acid;

β-[[[5,6,7,8-Tetrahydro-3-[2-(4-piperidinyl)E-ethenyl]-1,2,4-triazolo[4,3-a]pyridin-8-yl]carbonyl]amino]-βS-3-quinolinylpropanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-benzylsulfonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-3-pyridylacetylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-isobutyloxycarbonylamino-propanoic acid; or β-[[[3-[2-(4-piperidinyl)ethyl]-1,2,4-triazolo[4,3-a]pyridin-8-yl]carbonyl]amino]-βS-3-pyridylpropanoic acid;

and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

Further exemplifying the invention are methods of a) treating disorders mediated by GPIIb/IIIa, b) treating platelet-mediated thrombotic disorders, and/or c) inhibiting platelet aggregation in a subject in need thereof comprising administering to the subject a therapeutically effective amount of any of the compounds or pharmaceutical compositions described above.

Preferably, the therapeutically effective amount of the compound used in any of the methods of the present invention is about 0.1 to about 300 mg/kg/day.

Also included in the invention is the use of any of the compounds described above for the preparation of a medicament for a) treating disorders mediated by GPIIb/IIIa, b) treating platelet-mediated thrombotic disorders, and/or c) inhibiting platelet aggregation in a subject in need thereof.

DETAILED DESCRIPTION OF THE INVENTION

The present invention provides triazolopyridine compounds which are useful as antagonists of GPIIb/IIIa. More particularly, the compounds of formula (i) and (ii) inhibit the binding of fibrinogen to GPIIb/IIIa, and are therefore useful in treating platelet-mediated thrombotic disorders. Examples of platelet-mediated thrombotic disorders include, but are not limited to, arterial and/or venous thrombosis, acute myocardial infarction, re-occlusion following thrombolytic therapy and/or angioplasty, inflammation, unstable angina, restenosis, and a variety of vaso-occlusive disorders. These compounds are also useful as antithrombotics used in conjunction with fibrinolytic therapy (e.g., t-PA or streptokinase).

The triazolopyridine compounds of the present invention are GPIIb/IIIa antagonists. As demonstrated by the results of the pharmacological studies described hereinafter, the compounds show the ability to block fibrinogen binding to isolated GPIIb/IIIa ($IC_{50}$'s of ca. 0.0001–0.5 μM), inhibit platelet aggregation in vitro in the presence of a variety of platelet stimuli ($IC_{50}$'s of ca. 0.01–10 μM vs. thrombin), and furthermore, inhibit ex vivo platelet aggregation in animal models. Additionally, these agents exhibit efficacy in animal thrombosis models. The compounds of the present invention are triazolopyridines which show efficacy as antithrombotic agents by virtue of their ability to prevent platelet aggregation. Additionally, because the compounds of this invention inhibit integrin-mediated cell-cell or cell-matrix adhesion, they may be useful against restenosis, inflammation, bone resorption, tumor cell metastasis, etc. (D. Cox, *Drug News & Perspectives* 1995, 8, 197).

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. The pharmaceutically acceptable salts generally take a form in which the nitrogen on the 1-piperidine (pyrrolidine, piperazine) substituent is protonated with an inorganic or organic acid. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides novel intermediates of the formula AA3'

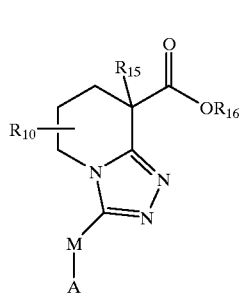

AA3' wherein M is $(CH_2)_m$, $CH=CH$, $CF=CH$, $CH=CF$ or $C\equiv C$; preferably, $(CH_2)_m$, $CH=CH$, or $C\equiv C$;

A is selected from piperidin-2-yl, piperidin-3-yl, piperidin-4-yl, piperazin-1-yl, pyrrolidin-2-yl, pyrrolidin-3-yl, $NHR_2$ or

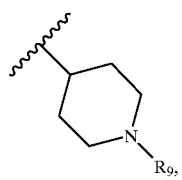

wherein $R_9$ is selected from hydrogen, $C_1$–$C_8$ alkyl, $CH=(NH)$, $CMe=(NH)$, $C_2$–$C_6$ acyl, $C_1$–$C_8$ alkoxycarbonyl or $ar(C_1$–$C_8$ alkoxy)carbonyl;

$R_2$ is selected from hydrogen, $C_1$–$C_8$ alkyl or $C_2$–$C_8$ acyl;

$R_{10}$ is selected from hydrogen or $C(O)N(R_1)YZ$, wherein $R_1$ is selected from hydrogen, $C_1$–$C_8$ alkyl or $C_3$–$C_8$ cycloalkyl;

Y is selected from $(CH_2)_p$, $CH(R_3)(CH_2)_q$, $(CH_2)_qCH(R_3)$, $(CH(CO_2R_4)CH_2)_q$, $(CH_2)_qCHOH$ or piperidine-3-carboxylic acid;

$R_3$ is selected from $C_1$–$C_8$ alkyl, $C_2$–$C_8$ alkenyl, $C_2$–$C_8$ alkynyl, aryl, $ar(C_1$–$C_8)$alkyl or heteroaryl;

$R_4$ is selected from hydrogen, $C_1$–$C_8$ alkyl or $C_3$–$C_8$ cycloalkyl;

p is an integer selected from 2 or 3;

q is an integer selected from 1, 2, or 3;

Z is $CO_2R_8$;

$R_8$ is hydrogen, $C_1$–$C_8$ alkyl, or $CH_2C(O)NR_{11}R_{12}$; wherein $R_{11}$ and $R_{12}$ are each independently selected from hydrogen, $C_1$–$C_8$ alkyl, or $C_3$–$C_8$ cycloalkyl;

m is an integer selected from 1, 2, or 3;

$R_{15}$ and $R_{16}$ are each independently selected from hydrogen or $C_1$–$C_8$ alkyl;

and salts thereof. Preferably, the intermediates have the formula

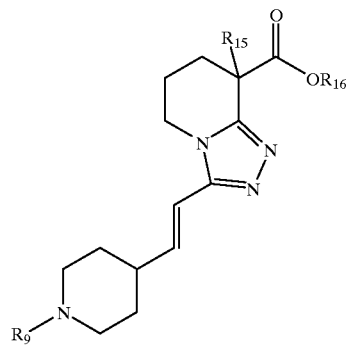

and salts thereof.

The present invention also provides a process for forming a compound of the formula (I) and pharmaceutically acceptable salts thereof, (I)

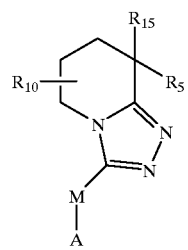

comprising reacting a compound of the formula AA3'

AA3'

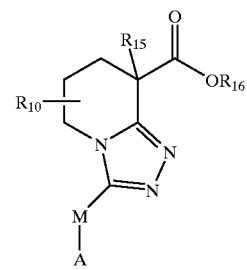

with a compound of the formula $H_2N$-$Q(CHW)CO2R8$ (AA4') to form the compound of the formula (1). Preferably, the process further comprises dissolving a compound of formula AA2'

AA2'

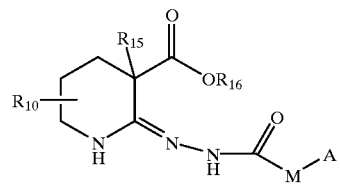

in a solvent selected from an alcohol, or aromatic such as chlorobenzene or toluene to form a solution, and heating the solution to form the compound AA3'

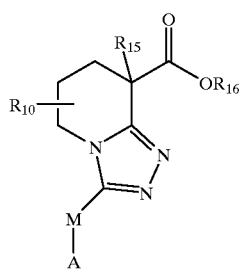

AA3'

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 carbons. Similarly, alkenyl and alkynyl groups include straight and branched chain alkenes and alkynes having 1 to 8 carbon atoms, or any number within this range.

The term "aryl" indicates aromatic groups such as phenyl and naphthyl.

The term "heteroaryl" as used herein represents a stable five or six membered monocyclic aromatic ring system or a nine or ten membered benzo-fused heteroaromatic ring system which consists of carbon atoms and from one to three heteroatoms selected from N, O or S. The heteroaryl group may be attached at any heteroatom or carbon atom which results in the creation of a stable structure. Examples of heteroaryl groups include, but are not limited to pyridyl, thienyl, furanyl, imidazolyl, isoxazolyl, oxazolyl, pyrazolyl, pyrrolyl, thiazolyl, thiadiazolyl, triazolyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl. Preferred heteroaryl groups include pyridyl, thienyl, furanyl and quinolinyl. When the heteroaryl group is "substituted heteroaryl", the substituent is one to three $C_1$–$C_8$ alkyl groups.

The term "aralkyl" means an alkyl group substituted with an aryl group (e.g., benzyl, phenylethyl). Similarly, the term "aralkoxy" indicates an alkoxy group substituted with an aryl group (e.g., benzyloxy).

The term "acyl" as used herein means an organic radical having 2 to 6 carbon atoms (branched or straight chain) derived from an organic acid by removal of the hydroxyl group.

It is intended that the definition of any substituent or variable (e.g., $R_8$) at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

Under standard nomenclature used throughout this disclosure, the terminal portion of the designated side chain is described first, followed by the adjacent functionality toward the point of attachment. Thus, for example, a "phenyl$C_1$–$C_6$ alkylamido$C_1$–$C_6$alkyl" substituent refers to a group of the formula:

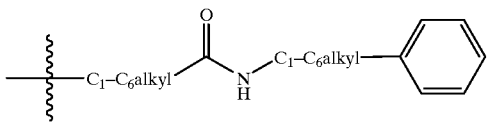

As used herein, the term "composition" is intended to encompass a product comprising the specified ingredients in the specified amounts, as well as any product which results, directly or indirectly, from combinations of the specified ingredients in the specified amounts.

The utility of the compounds to treat thrombotic disorders can be determined according to the procedures described in Examples 21 to 23 herein. The present invention therefore provides a method of treating thrombotic disorders in a subject in need thereof which comprises administering any of the compounds as defined herein in a quantity effective to treat thrombotic disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of formula (I) or (II) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effect dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be seperated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehides. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-I-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiey & Sons, 1991. The protecting groups may be removed at a convenient subsequent stage using methods known from the art.

The method of treating thrombotic disorders described in the present invention may also be carried out using a pharmaceutical composition comprising any of the compounds as defined herein and a pharmaceutically acceptable carrier. The pharmaceutical composition may contain between about 0.01 mg and 100 mg, preferably about 5 to 50 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprejactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of thrombotic disorders is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 100 mg/kg of body weight per day. Preferably, the range is from about 0.03 to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, induding patient age, weight, diet and time of administration, will result in the need to adjust dosages.

Abbreviations used in the instant specification, particularly the Schemes and Examples, are as follows:
AcOH=Acetic acid
Bn or Bzl=Benzyl
Boc=t-Butoxycarbonyl
BOC-ON=2-(t-Butoxycarbonyloxyimino)-2-Phenylacetonitrile
BOP-Cl=Bis(2-oxo-3-oxazolidinyl)-phosphinic chloride
BSA=bovine serum albumin
CBZ=Benzyloxycarbonyl
CP=compound
DCE=1,2-Dichloroethane
DCM=Dichloromethane
DIC=Diisopropylcarbodiimide
DIEA=Diisopropylethylamine
DMAP=4-Dimethylaminopyridine
DMF=N,N-Dimethylformamide
DMSO=Dimethylsulfoxide
EDC=Ethyl dimethylaminopropyl-Carbodiimide
EDTA=Ethylenediaminetetraacetic acid
Et=Ethyl
Et$_2$O=Diethyl ether
EtOAc=ethyl acetate
EtOH=ethanol
HBTU=2-(1H-Benzotriazole-1-yl)- 1,1,3,3-tetramethyluronium hexafluorophosphate
HEPES=4-(2-Hydroxyethyl)-1-piperazine-ethanesulfonic acid
HOBT=Hydroxybenzotriazole
i-Pr=Isopropyl
Me=methyl
MeOH=methanol
MPK=milligrams per kilogram
NMM=N-Methylmorpholine
Nip=Nipecotyl (unless noted otherwise, racemic at 3-position)
NT=not tested
Ph=phenyl
PPT=precipitate
PTSA=p-Toluenesulfonic acid
RT=room temperature
sat'd=saturated
TEA=triethylamine
TFA=Trifluoroacetic acid
THF=Tetrahydrofuran
TMS=trimethylsilane
Z=Benzyloxycarbonyl Particularly preferred compounds of the present invention include those compounds shown in Table I. Where it is noted, the letter "R" indicates the absolute configuration (Cahn-Ingold-Prelog rules).

TABLE I

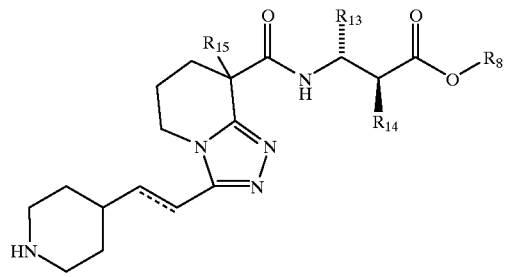

| # | R$_8$ | R$_{13}$ | R$_{14}$ | R$_{15}$ | Bond |
|---|---|---|---|---|---|
| 1 | H | 3-pyridyl | H | H | single |
| 2 | H | H | H | H | single |
| 3 | H | H | NHCO$_2$CH$_2$Ph | H | single |
| 4 | CH$_2$CONEt$_2$ | 3-pyridyl | H | H | single |
| 5 | H | H | NHCO$_2$CH$_2$Ph | H | double |
| 6 | CH$_2$CONEt$_2$ | H | NHCO$_2$CH$_2$Ph | H | single |
| 7 | H | 3-thienyl$^a$ | H | H | single |
| 8 | H | H | NHCO$_2$CH$_2$Ph | Me | single |
| 9 | See structure below | | | | |
| 10 | H | 4-pyridyl$^a$ | H | H | double |
| 11 | H | H | NHSO$_2$-3,5-Me$_2$-4-isoxazolyl | H | double |
| 12 | H | 3-pyridyl | H | H | double |
| 13 | H | 3-quinolinyl | H | H | double |
| 14 | H | H | NHSO$_2$CH$_2$Ph | H | double |

TABLE I-continued

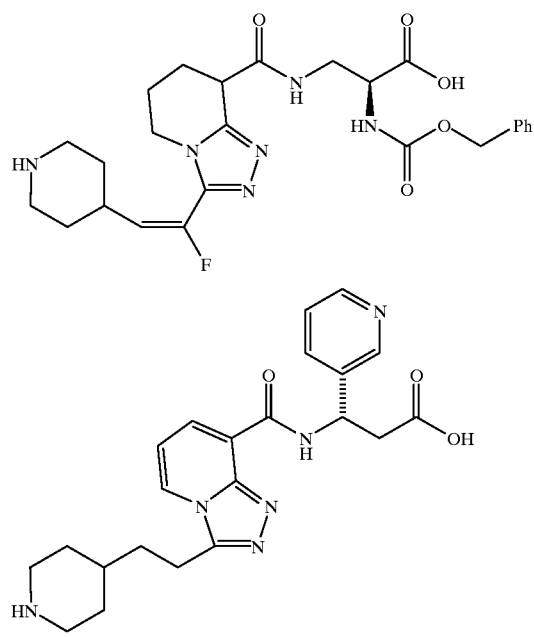

| # | $R_8$ | $R_{13}$ | $R_{14}$ | $R_{15}$ | Bond |
|---|---|---|---|---|---|
| 15 | H | H | NHCOCH$_2$-3-pyridyl | H | double |
| 16 | H | H | NHCO$_2$CH$_2$CHMe$_2$ | H | double |
| 17 | See structure below | | | | | a. Racemic.

The compounds of the invention wherein $R_{10}$ is H, $R_5$ is C(O)NHQ(CHW)$_r$CO$_2$R$_8$, and A is piperidin-4-yl, may be prepared as shown in Scheme AA. Intermediate AA4 was prepared as detailed in PCT International Application WO 97/41102 and as published (J. Rico, *J. Org. Chem.* 1993, 58, 7948). Carboxylic acid AA3 was prepared in four steps starting with O-ethylation of AA1 with triethyloxonium tetrafluoroborate, condensation with N-CBZ-4-piperidinepropanoyl hydrazide (prepared from 4-piperidinepropanoic acid and hydrazine/HBTU as described in PCT Int'l. Appl. WO 97/41102), and then cyclization of amridazone AA2 via methanoiic reflux. For compounds 3, 4, and 6–8, N-Boc-4-piperidinepropanoyl hydrazide (preparation in PCT Int'l. Appl. WO 97/41102) was employed in the reaction with O-ethylated AA1. Next, the triazole ethyl ester was saponified with lithium hydroxide to afford AA3. Standard amide bond coupling conditions were employed using β-amino esters such as AA4 and AA3 with HBTU, and HOBT in acetonitrile. Compound 2 were prepared as shown for 1; resolved β-amino ester starting materials (see AA4 experimental) were prepared as shown for AA4.

SCHEME AA

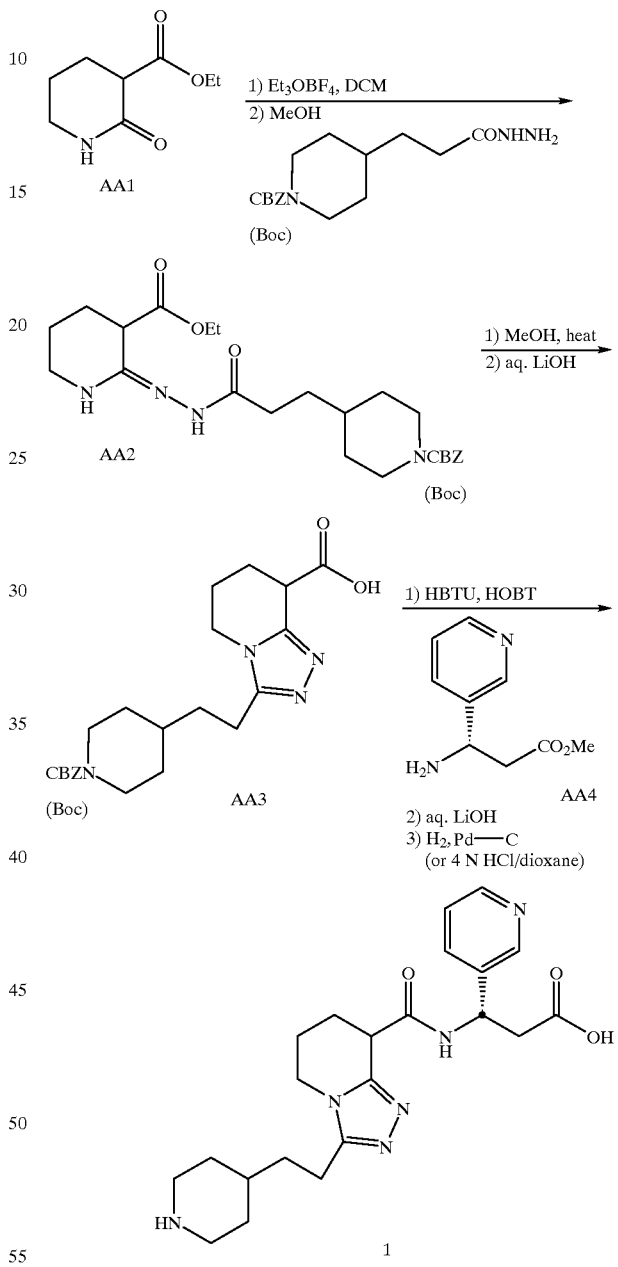

2-Chloro-N,N-diethylacetamide was purchased from Aldrich Chemical Company. Chloroacetamides may be prepared in one step from 2-chloroacetyl chloride and the appropriate amine (Scheme AB; K. Krakowiak, *J. Heterocyclic Chem.* 1989, 26, 661.). In this procedure, 2-chloroacetyl chloride and aq. sodium hydroxide were added dropwise to a solution of amine/DCM at RT and reacted over a 1–2 h period.

SCHEME AB

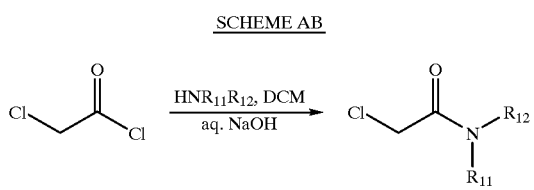

To prepare the compounds where A is N-alkyl-piperidine ($R_9$=alkyl), compound 1, for example, was treated with aldehyde/sodium cyanoborohydride in ethanol to give the N-alkylpiperidine. Formamidinopiperidines were prepared by treating compound 1, for example, with ethyl formimidate.HCl in ethanol; the corresponding acetamidinopiperidines were prepared using S-2-naphthylmethyl thioacetimidatee•HCl in ethanol (B. Shearer, *Tetrahedron Lett.* 1997, 38, 179).

SCHEME AC

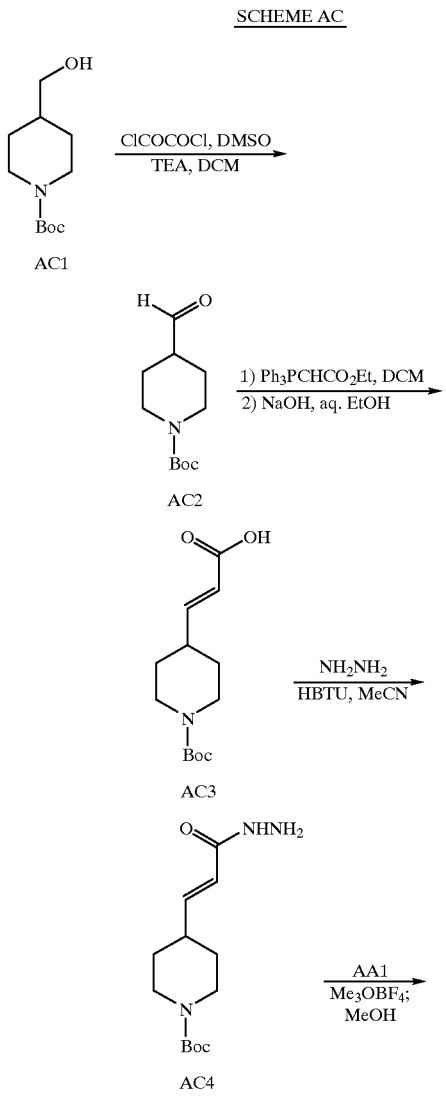

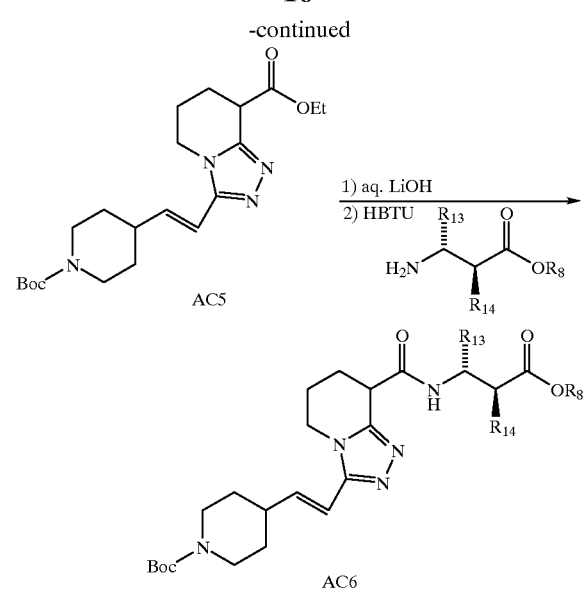

Intermediate N-Boc-4-piperidinepropenoic acid AC3 may be prepared as shown in Scheme AC. Alcohol AC1 was oxidized to the corresponding aldehyde AC2 using standard Swern conditions (oxalyl chloride/DMSO). AC2 was converted to the olefinic ester using the Wittig reagent in dichloromethane. This ester was then saponified to the acid in sodium hydroxide to afford AC3. AC3 was converted to the corresponding hydrazide (AC4; hydrazine/HBTU) and employed to prepare intermediates AC6 as described in Scheme AA. Intermediates AC6 was carried forward by lithium hydroxide saponification and then HCl-mediated saponification to give olefinic products such as 5, and 10–16.

SCHEME AD

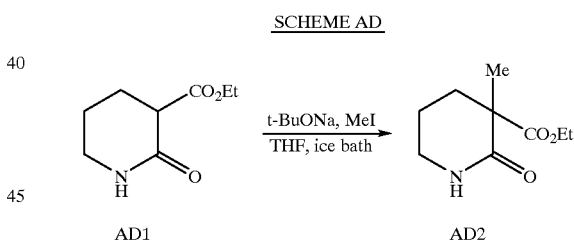

Compounds where $R_{15}$ is alkyl may be prepared as shown in Scheme AD using standard alkylating methods. Alkylated intermediate AD2 can then be converted to triazolopyridine targets as shown in Scheme AA.

Compounds where M is ethynyl were prepared by displacement of N-Boc-4-methanesulfonyloxypiperidine with potassium ethyl propiolate (potassium carbonatelethyl propiolate) to give methyl N-Boc-piperidineprop-3-ynoate (T. Jeffery, *Tetrahedron Lett.* 1989, 30, 2225). This ester was then saponified to the corresponding carboxylic acid and coupled with hydrazine using HBTU.

Compounds where $R_{10}$ is C(O)N($R_1$)YZ and $R_5$ is H are prepared according to the method described in Scheme AA using an appropriately substituted triazolopyridine as the starting material.

SCHEME AE

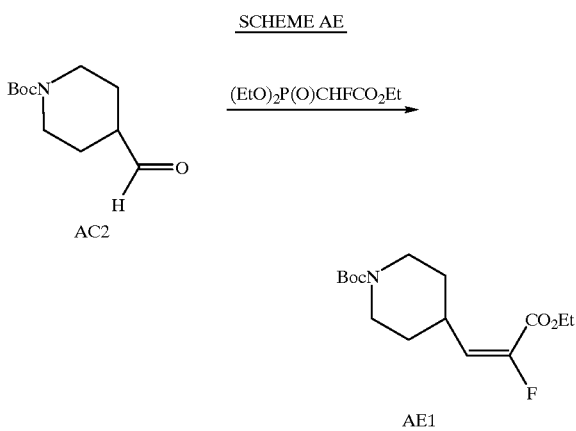

Vinyl fluoride intermediates AE1 may be prepared using Homer-Emmons methodology as shown in Scheme AE. Herein, the aldehyde AC2 was reacted with triethyl 2-fluorophosponoacetate/DBU/lithium chloride to afford ester AE1. The ester was then carried forward as described in Scheme AA to give vinyl fluoride antagonists (see 9).

SCHEME AF

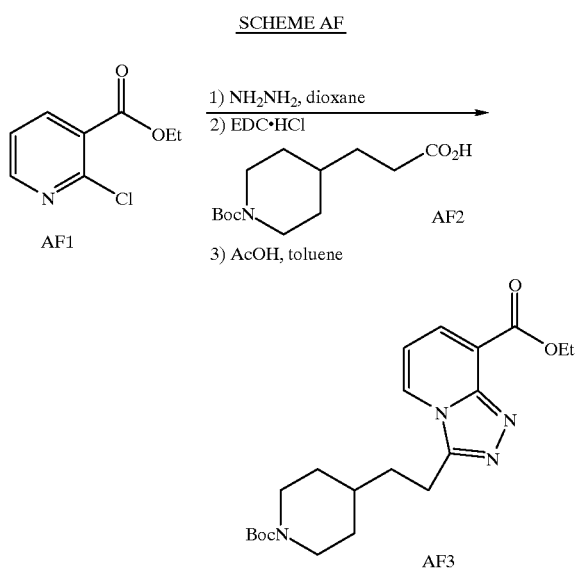

Unsaturated triazolopyridine compounds such as 17 may be prepared as shown in Scheme AF. Herein, chloronicotinate AF1 was reacted with hydrazine to afford a hydrazinopyridine intermediate, which was then condensed with EDC-activated AF2 to afford an acyl hydrazide intermediate. This material was heated in the presence of acetic acid to cyclize to AF3. Intermediate AF3 was then carried forward to final material 17 as described in Scheme AA.

The following Examples are set forth to aid in the understanding of the invention, and are not intended and should not be construed to limit in any way the invention set forth in the claims which follow thereafter.

Protected amino acids were purchased from Aldrich Chemical or Bachem Bioscience Inc. N-α-CBZ-L-diaminopriopionic acid was purchased from Fluka. Ethyl 2-oxo-3-piperidine-carboxylate was purchased from Aldrich Chemical Company, as were all other chemicals. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, inc., Madison, N.J. and are expressed in percentage by weight of each element per total molecular weight. In those cases where the product is obtained as a salt, the free base is obtained by methods known to those skilled in the art, e.g. by basic ion exchange purification. Nuclear magnetic resonance (NMR) spectra for hydrogen atoms were measured in the indicated solvent with tetramethylsilane (TMS) as the internal standard on a Bruker AM-360 (360 MHz) spectrometer. The values are expressed in parts per million down field from TMS. The mass spectra (MS) were determined on a Finnigan 3300 spectrometer (methane), using desorption chemical ionization techniques. Unless otherwise noted, the materials used in the examples were obtained from readily available commercial suppliers or synthesized by standard methods known to anyone skilled in the art of chemical synthesis. The substituent groups, which vary between examples, are hydrogen unless otherwise noted.

EXAMPLE 1

Methyl (S)-3-amino-3-(3-pyridyl) propionate•2HCl (AA4)

A mixture of 3-pyridinecarboxaldehyde (0.47 mol), EtOH (100 mL), NH$_4$OAc (0.47 mol), and malonic acid (0.70 mol) was heated at reflux for 6 h, cooled, and filtered. The white solid was washed with EtOH and MeOH and dried (E. Profft, *J. Prakt. Chem.* 1965, 30, 18). This solid was dissolved in 2:1 acetone/water (360 mL), treated with triethylamine (0.72 mol) and phenylacetyl chloride (0.36 mol), and stirred for 22 h. The mixture was evaporated and the residue dissolved in water (500 mL) and adjusted to pH 12 (1 N NaOH). The aqueous layer was adjusted to pH 2 (conc. HCl), extracted with Et$_2$O, and evaporated to a white foam. The foam was purified by silica gel chromatography (10% MeOH/DCM) to give racemic 3-phenylacetamido-3-(3-pyridyl)propionic acid. A solution of this compound (0.22 mol) in water (600 mL) at RT was adjusted to pH 7.5 using KOH (3.0 N) and treated with penicillin amidase (91520 units, Sigma). This mixture was stirred for 47 h, acidified to pH 1 with HCl (conc), and the resultant ppt filtered through Celite. The filtrate was extracted with Et$_2$O (3×300 mL), concentrated in vacuo, and treated with MeOH/conc. NH$_4$OH (9:1). This product-containing solution was purified by silica gel chromatography (eluent DCM/MeOH/NH$_4$OH, 78:18:4) to give (S)-3-phenylacetamido-3-(3-pyridyl) propionic acid ammonium salt. This product was treated with HCl (6.0 N, 292 mL), heated at reflux for 5 h, cooled to RT, and extracted with Et$_2$O (3×200 mL). The aqueous layer was adjusted to pH 12, concentrated in vacuo, and the resultant solid triturated with MeOH (2×300 mL). This solution was evaporated to give the sodium salt. This material was treated with MeOH (500 mL), 2,2-dimethoxypropane (44 mL), and HCl (4 N in dioxane, 84 mL), and stirred for 90 h at RT. This mixture was filtered and the filtrate concentrated in vacuo. The resultant off-white solid was triturated with Et$_2$O (2×150 mL) and dried to give compound AA4 (96% ee) as a white, amorphous solid.

EXAMPLE 2

β-[[[5,6,7,8-Tetrahydro-3-[2-(4-piperidinyl)ethyl]-1,2,4-triazolo[4,3-a]pyridin-8-yl]carbonyl]amino]-βS-3-pyridinepropanoic acid (1)

Triethyloxonium tetrafluoroborate (11.7 mL, 1.0 M in DCM) was added to a solution of ethyl 2-oxo-3-piperidinecarboxylate (AA1, 2.0 g, 11.7 mmol) in DCM (5.7 mL) and stirred for 4 h. N-CBZ-4-piperidine-propionic hydrazide (3.6 g, 11.8 mmol) dissolved in DCM (7.3 mL) was added and the resulting mixture was stirred for 18 h. The mixture was diluted with DCM (100 mL) and washed with sat'd sodium chloride (40 mL). The organic layer was dried (sodium sulfate) and evaporated to give a white solid (AA2). The solid was dissolved in MeOH (200 mL) and refluxed for 6 h. The mixture was cooled and evaporated. The white solid was again dissolved in MeOH (200 mL) and refluxed 20 h. The mixture was cooled and evaporated to give a white solid. This white solid (2.2 g) was dissolved in THF (5 mL), cooled to 0° C., and treated with aq. LiOH (0.21 g in 2.0 mL water). The reaction was stirred for 1 h to give AA3•Li, and MeCN (50 mL) was added followed by AA4 (1.5 g), HBTU (3.8 g), HOBT (1.1 g), and NMM (1.2 mL). The mixture was stirred for 20 h, diluted with DCM (100 mL), washed with sat'd ammonium chloride (30 mL), and the layers were separated. The organic layer was dried (sodium sulfate) and evaporated. The crude mixture was purified by neutral alumina chromatography (eluent: DCM/MeOH, 98/2) to give the methyl ester. The methyl ester was dissoved in THF (28 mL), cooled to 0° C., and treated with aq. LiOH (0.18 g in 70 mL water). The reaction was stirred for 1 h, acidified with acetic acid (4 mL), and extracted with DCM (3×50 mL). The combined organics were dried (sodium sulfate) and evaporated to afford the corresponding carboxylic acid. The acid (0.65 g) was dissolved in dioxane (30 mL) and water (30 mL). 5% palladium on carbon (0.11 g) was added and the mixture was hydrogenated with 50 psi hydrogen for 0.5 h. The mixture was filtered through celite, washed with water (10 mL) and ethyl acetate (20 mL). The layers were separated and the aqueous layer was lyophilized to give a white solid (1): mp 97–100° C. $^1$H NMR (DMSO-$d_6$) δ 8.99 (t, 1 H), 8.55 (m, 1 H), 8.41 (m, 1 H), 7.75 (t, 1 H), 7.23–7.39 (m, 2 H), 5.16 (t, 1 H), 3.78–3.91 (m, 2 H), 3.09–3.55 (m, 4 H), 2.57–2.84 (m, 4 H), 1.97–2.10 (m, 2 H), 1.76–1.91 (m, 3 H), 1.56–1.71 (m, 2 H), 1.15–1.51 (m, 3 H); MS m/e 427 (MH$^+$).

EXAMPLE 3

β-[[[5,6,7,8-Tetrahydro-3-[2-(4-piperidinyl)ethyl]-1, 2,4-triazolo[4,3-a]pyridin-8-yl]carbonyl]amino]-β-propanoic acid (2)

Intermediate AA3 (0.90 mmol) and β-Ala-OMe (0.90 mmol) were coupled using HBTU/HOBT and the product carried forward to give 2 as described in example 1. Compound 2 was isolated as white flakes: mp 86–90° C. $^1$H NMR (DMSO-$d_6$) δ 3.89–3.99 (m, 1 H), 3.31–3.49 (m, 3 H), 2.89–3.08 (m, 3 H), 2.83 (t, 1 H), 2.38 (t, 1 H), 2.12–2.28 (m, 4 H), 1.89–2.08 (m, 4 H), 1.73–1.80 (m, 1 H), 1.56–1.63 (m, 2 H), 1.39–1.50 (m, 4 H); MS m/e 350 (MH$^+$).

EXAMPLE 4

β-[[[5,6,7,8-Tetrahydro-3-[2-(4-piperidinyl)ethyl]-1, 2,4-triazolo[4,3-a]pyridin-8-yl]carbonyl]amino]-αS-benzyloxycarbonylamino-propanoic acid (3)

Intermediate AA3 (N-Boc derivative was employed and deprotected with 4 N HCl in dioxane at the end of the synthesis, 0.80 mmol) and N$^α$-Cbz-Dpr-OMe (0.80 mmol) were coupled using HBTU/HOBT and the product carried forward to give 3 as described for compound 1. Compound 3 was isolated as white flakes: mp 142–145° C.; MS m/e 499 (MH$^+$). Anal. calcd. for $C_{25}H_{34}N_6O_5$•2.8 HCl•1.7 H$_2$O (631.30): C, 47.57; H, 6.42; N, 13.32; Cl, 15.73. Found: C, 47.20; H, 6.39; N, 13.70; Cl, 15.96.

EXAMPLE 5

β-[[[5,6,7,8-Tetrahydro-3-[2-(4-piperidinyl)ethyl]-1, 2,4-triazolo[4,3-a]pyridin-8-yl]carbonyl]amino]-βS-3-pyridinepropanoic acid 2-(Diethylamino)-2-oxoethyl ester (4)

Intermediate AA3 (N-Boc derivative was employed and deprotected with 4 N HCl in dioxane at the end of the synthesis, 1.0 mmol) and 3-amino-3-(3-pyridyl)propanoic acid 2-diethylamino-2-oxoethyl ester (1.0 mmol) were coupled using HBTU/HOBT and the product carried forward to give 4 as described for compound 1. 3-Amino-3-(3-pyridyl)propanoic acid 2-diethylamino-2-oxoethyl ester was prepared as follows. 3-N-Boc-amino-3-(3-pyridyl)propanoic acid (1.9 mmol; prepared using the same methods as its phenylacetamide derivative in example 2) was dissolved in EtOAc (50 mL) and TEA (0.3 mL) and treated with 2-Cl-N,N-diethylacetamide (0.60 mL). This mixture was stirred for 22 h, diluted with sat'd ammonium chloride (30 mL), and the layers separated. The organic layer was dried (sodium sulfate), evaporated, and purified by silica gel chromatography (8% EtOH/DCM) to afford a glass. The glass was treated with HCl (4 N in dioxane, 10 mL), stirred for 3 h, evaporated, and triturated with diethyl ether (50 mL) to give 3-amino-3-(3-pyridyl)propanoic acid 2-diethylamino-2-oxoethyl ester as a foamy dihydrochloride salt.

Compound 4 was isolated as a white powder: mp 110–113° C.; MS m/e 540 (MH$^+$). Anal. calcd. for $C_{28}H_{41}N_7O_4$•3.0 HCl•2.5 H$_2$O•0.7 dioxane (755.77): C, 48.95; H, 7.28; N, 12.97; Cl, 14.07. Found: C, 48.99; H, 7.09; N, 12.60; Cl, 13.69.

EXAMPLE 6

N-t-Butoxycarbonyl-4-piperidine-3-propenoic acid (AC3)

To a solution of oxalyl chloride (24.8 mL, 50 mmol) in DCM (200 mL) at −78° C. was added DMSO (7.0 mL) dropwise. The mixture was stirred for 30 min, treated with AC1 (8.2 gl 38 mmol), and stirred for 2 h. Triethylamine (31.7 mL) was added dropwise, the mixture was warmed to RT, and the mixture diluted with water (30 mL). The layers were separated; the organic layer was washed with sat'd ammonium chloride (30 mL) and sat'd sodium chloride (30 mL), dried (magnesium sulfate), evaporated, and purified by silica gel chromatography (20% EtOAc/hexane) to give AC2 as a white solid. A solution of ethyl 2-(triphenylphosphoranylidene)acetate (13.1 g, 38 mmol) and DCM (40 mL) at 5° C. was treated with AC2 (7.3 g), warmed to RT, stirred for 2.5 h, and evaporated to dryness. This solid was treated with pentane (50 mL), and triphenylphosphine oxide removed by filtration. The pentane solution was concentrated and the solid purified by silica gel chromatography (10% EtOAc/hexane) to afford a glass. The glass was dissolved in EtOH (60 mL) and this solution treated with water (60 mL) and sodium hydroxide (59 mL, 1.0 N) at RT. The mixture was stirred for 4 h, acidified with citric acid (8 g), and extracted with DCM (3×100 mL). The combined organics were dried (magnesium sulfate) and evaporated to give AC3 as a white solid. MS m/e 256 (MH$^+$).

EXAMPLE 7

β-[[[5,6,7,8-Tetrahydro-3-[2-(4-pipieridinyl)E-ethylene]-1,2,4-triazolo[4,3-a]pyridin-8-yl]carbonyl]amino]-αS-benzyloxycarbonylamino-propanoic acid (5)

Intermediate AC3 (11.2 g, 45 mmol), anhydrous hydrazine (45 mmol), HBTU (60 mmol), HOBT (60 mmol), MeCN (200 mL), and NMM (90 mmol) were stirred at 5° C. for 4 h. The mixture was diluted with DCM (200 mL), washed with sard ammonium chloride (50 mL), and the layers were separated. The organic layer was dried (sodium sulfate) and evaporated to give AC4. DCM (100 mL), trimethyloxonium tetrafluorborate (6.6 g), and AA1 (7.6 g) were stirred at rt for 4 h, treated with AC4 (dissolved in 30 mL DCM) and stirred for 21 h. The mixture was diluted with DCM (200 mL), and washed with sat'd sodium chloride (30 mL). The organic layer was dried (sodium sulfate) and evaporated. The residue was dissolved in MeOH (420 mL) and refluxed for 24 h. The mixture was cooled and evaporated to give a white solid. This white solid was dissolved in THF (10 mL), cooled to 0° C., and treated with aq. LiOH monohydrate (0.96 g in 10 mL water). The reaction was stirred for 6 h, and MeCN (200 mL) was added followed by methyl αS-benzyloxycarbonylamino-propanoate hydrochloride (6.0 g), HBTU (16 g), HOBT (3.1 g), and NMM (5.0 mL). The mixture was stirred for 20 h cold, diluted with DCM (100 mL), washed with sat'd ammonium chloride (30 mL), and the layers were separated. The organic layer was dried (sodium sulfate) and evaporated. The crude mixture was purified by neutral alumina chromatography (eluent: DCM/MeOH, 99/1) to give the methyl ester AC6. The methyl ester was dissolved in THF (28 mL), cooled to 0° C., and treated with aq. LiOH monohydrate (0.25 g in 100 mL water). The reaction was stirred for 1 h, acidified with acetic acid (15 mL), and extracted with $Et_2O$/THF (1:1, 150 mL). The combined organics were dried (sodium sulfate) and evaporated to afford the corresponding carboxylic acid. The carboxylic acid was treated with dioxane (16 mL) and HCl (12 mL, 4 N in dioxane), stirred for 7 h, and evaporated to a foam. The foam was triturated with warm MeCN (50 mL) and $Et_2O$ (100 mL), and dried to give compound 5 as white flakes: mp 86–90° C.; MS m/e 497 (MH$^+$). Anal. calcd. for $C_{25}H_{32}N_6O_5$•1.7 HCl•2.5 $H_2O$•0.3 dioxane (630.02): C, 49.95; H, 6.58; N, 13.34; Cl, 9.57. Found: C, 50.13; H, 6.56; N, 12.98: Cl, 9.64.

EXAMPLE 8

β-[[[5,6,7,8-Tetrahydro-3-[2-(4-piperidinyl)ethyl]-1, 2,4-triazolo[4,3-a]pyridin-8-yl]carbonyl]amino]-αS-benzyloxycarbonylamino-propanoic acid 2-(Diethylamino)-2-oxoethyl ester (6)

Intermediate AA3 (N-Boc derivative was employed and deprotected with 4 N HCl in dioxane at the end of the synthesis, 1.0 mmol) and N$^α$-Cbz-Dpr 2-diethylamino-2-oxoethyl ester (prepared from N$^α$-Cbz-Dpr(Boc)-OH and 2-Cl-diethylacetamide as described for compound 4, 1.0 mmol) were coupled using HBTU/HOBT and the product carried forward to give 6 as described for compound 1. Compound 6 was isolated as a white powder: mp 108–111° C.; MS m/e 612 (MH$^+$). Anal. calcd. for $C_{31}H_{45}N_7O_6$•2.2 HCl•0.5 $H_2O$•0.4 dioxane (736.21): C, 53.19; H, 7.04; N, 13.32; Cl, 10.59. Found: C, 53.37; H, 7.20; N, 13.00; Cl, 10.60.

EXAMPLE 9

β-[[[5,6,7,8-Tetrahydro-3-[2-(4-piperidinyl)ethyl]-1, 2,4-triazolo[4,3-a]pyridin-8-yl]carbonyl]amino]-β-3-thiophenepropanoic acid (7)

Intermediate AA3 (N-Boc derivative was employed and deprotected with 4 N HCl in dioxane at the end of the synthesis, 1.5 mmol) and 3-amino-3-(3-thienyl)propanoic acid (1.5 mmol) were coupled using HBTU/HOBT and the product carried forward to give 7 as described for compound 1. Compound 7 was isolated as a white powder: mp 127–131° C.; MS m/e 432 (MH$^+$). Anal. calcd. for $C_{21}H_{29}N_5O_3S$•2.4 HCl•1.7 $H_2O$•0.4 dioxane (584.93): C, 46.41; H, 6.55; N, 11.97; Cl, 14.55. Found: C, 46.58; H, 6.58; N, 11.64; Cl, 14.56.

EXAMPLE 10

β-[[[5,6,7,8-Tetrahydro-8-methyl-3-[2-(4-piperidinyl)ethyl]-1,2,4-triazolo[4,3-a]pyridin-8-yl] carbonyl]amino]-αS-benzyloxycarbonylamino-protanoic acid (8)

Compound 8 was prepared using the methods described for 3 except 8-methyl intermediate AD2 (3.0 mmol) was employed rather than AA1 in the reaction with Meerwein's reagent (3.0 mmol) and then N-Boc-4-piperidinepropanoyl hydrazide (3.0 mmol). Compound 8 was isolated as off-white flakes: mp 140–143° C.; MS m/e 513 (MH$^+$). Anal. calcd. for $C_{26}H_{36}N_6O_5$•2.9 HCl•1.9 $H_2O$ (652.58): C, 47.86; H, 6.60; N, 12.88; Cl, 15.76. Found: C, 47.76; H, 7.00; N, 13.22; Cl, 16.03.

EXAMPLE 11

β-[[[6,7,8-Tetrahydro-3-[2-(4-piperidinyl)Z-1-fluoroethylene]-1,2,4-triazolo[4,3-a]pyridin-8-yl] carbonyl]amino]-αS-benzyloxycarbonylamino-propanoic acid (9)

Compound 9 was prepared using the methods described in Scheme AE. Intermediate AE1 was prepared as follows. Lithium chloride (0.39 g) was added to a solution cooled to 0° C. of triethyl-2-fluoro-2-phophonoacetate (1.84 mL) and 1,8-diazabicyclo[5.4.0]undec-7-ene (1.15 mL) in acetonitrile (6 mL). The mixture was stirred until the lithium chloride was dissolved to form a homogeneous solution. N-Boc-piperidine-4-carboxaldehyde (1.61 g) in acetonitrile (2.0 mL) was added to the mixture and stirred for 24 h at room temperature. The reaction was quenched with saturated ammonium chloride (20 mL), diluted with ethyl acetate (150 mL), and washed with saturated sodium chloride (50 mL). The organic layer was dried (magnesium sulfate) and evaporated to yield 2.27 g of (E)-ethyl 2-fluoro-3-(N-Boc-piperdin-4-yl)propenoate (AE1). AE1 was carried forward as shown in Scheme AA to afford 9. Compound 9 was isolated as white flakes: mp 147–150° C.; MS m/e 515 (MH$^+$). Anal. calcd. for $C_{25}H_{31}FN_6O_5$•2.3 HCl•1.6 $H_2O$ (627.25): C, 47.88; H, 5.87; N, 13.40; Cl, 13.00. Found: C, 48.26; H, 6.02; N, 12.90; Cl, 12.74.

EXAMPLE 12

β-[[[5,6,7,8-Tetrahydro-3-[2-(4-piperidinyl)E-ethylene]-1,2,4-triazolo[4,3-a]pyridin-8-yl]carbonyl] amino]-β-4-pyridinepropanoic acid (10)

Compound 10 was prepared as described for compound 5 from intermediate AC3 (1.5 mmol) and methyl 3-amino-3-(4-pyridyl)propanoate (1.0 mmol). Compound 10 was isolated as yellow flakes: mp 235° C.; MS m/e 425 (MH$^+$). Anal. calcd. for $C_{22}H_{28}N_6O_3$•3.1 HCl•3.0 $H_2O$ (635.63): C, 45.35; H, 6.52; N, 13.22; Cl, 17.29. Found: C, 45.67; H, 6.59; N, 12.94; Cl, 17.30.

EXAMPLE 13

β-[[[5,6,7,8-Tetrahydro-3-[2-(4-piperidinyl)E-ethylene]-1,2,4-triazolo[4,3-a]pyridin-8-yl]carbonyl] amino]-αS-4-(3,5-dimethylisoxazolyl) sulfonylamino-propanoic acid (11)

Compound 11 was prepared as described for compound 5 from intermediate AC3 (4.0 mmol) and methyl 3-amino- αS-4-(3,5-dimethylisoxazolyl)sulfonylaminopropanoate (3.0 mmol). Compound 11 was isolated as a glass: mp 145–148° C.; MS m/e 522 (MH+). Anal. calcd. for $C_{22}H_{31}N_7O_6S$•2.8 HCl•2.0 $H_2O$•0.5 dioxane (703.78): C, 40.96; H, 5.99; N, 13.93; Cl, 14.11. Found: C, 40.63; H, 5.82; N, 14.00; Cl, 13.11.

EXAMPLE 14

β-[[[5,6,7,8-Tetrahydro-3-[2-(4-piperidinyl)E-ethylene]-1,2,4-triazolo[4,3-a]pyridin-8-yl]carbonyl] amino]-βS-3-pyridylpropanoic acid (12)

DCM (100 mL), trimethyloxonium tetrafluorborate (3.0 g), and AA1 (2.0g) were stirred at rt for 24 h, treated with AC4 (5.4 g, dissolved in 17 mDCM) and stirred for 24 h. The mixture was diluted with DCM (100 mL), and washed with sat'd sodium chloride (50 mL). The organic layer was dried (magnesium sulfate) and evaporated. The yellow foam was dissolved in MeOH (179 mL) and refluxed for 24 h. The mixture was cooled, evaporated, and purified over silical gel (MeOH/DCM/$NH_4OH$, 5:94:1) to give a solid. This solid was dissolved in THF (7 mL), cooled to 0° C., and treated with aq. LiOH monohydrate (0.89 g in 19 mL water). The reaction was stirred for 6 h, and MeCN (190 mL) was added followed by AA4 hydrochloride (4.8 g), HBTU (13.5 g), HOBT (2.6 g), and NMM (4.7 mL). The mixture was stirred for 20 h cold, diluted with DCM (300 mL), washed with water (100 mL), and the layers were separated. The organic layer was dried (magnesium sulfate) and evaporated. The crude mixture was purified by neutral alumina chromatography (eluent DCM/MeOH, 99/1) to give the methyl ester AC6. The methyl ester was dissolved in THF (46 mL), cooled to 0° C., and treated with aq. LiOH monohydrate (0.29 g in 116 mL water). The reaction was stirred for 0.5 h, acidified with acetic acid (15 mL), and extracted with DCM (300 mL). The combined organics were dried (magnesium sulfate) and evaporated to afford the corresponding carboxylic acid. The carboxylic acid was treated with dioxane (20 mL) and HCl (3 mL, 4 N in dioxane), stirred for 1 h, and evaporated to a foam. The foam was triturated with warm MeCN (50 mL) and $Et_2O$ (100 mL), and then lyophilized from water to give compound 12 as clear flakes: mp 134–137° C. $^1H$ NMR (DMSO-$d_6$) δ 9.55–9.59 (m, 1 H), 8.94–9.24 (m, 2 H), 8.81 (d, 1 H), 8.53–8.65 (m, 1 H), 8.01–8.04 (m, 1 H), 7.02–7.09 (m, 1 H), 6.54 (d, 1 H), 5.29–5.35 (m, 1 H), 4.11–4.26 (m, 2 H), 3.26–3.49 (m, 2 H), 2.93–3.00 (m, 3 H), 2.63–2.69 (m, 1 H), 1.91–2.43 (m, 8 H), 1.65–1.69 (m, 2 H); MS m/e 425 (MH+). Anal. calcd. for $C_{22}H_{28}N_6O_3$•2.8 HCl•3.2 $H_2O$ (562.62): C, 47.08; H, 6.25; N, 14.72; Cl, 17.69. Found: C, 47.00; H, 6.09; N, 14.37; Cl, 17.82.

EXAMPLE 15

β-[[[5,6,7,8-Tetrahydro-3-[2-(4-piperidinyl)E-ethylene]-1,2,4-tiazolo[4,3-a]pyridin-8-yl]carbonyl] amino]-βS-3-quinolinylpropanoic acid (13)

Compound 13 was prepared as described for compound 5 from intermediate AC3 (3.0 mmol) and methyl 3-amino-3S-(3-pyridyl)propanoate (2.4 mmol). Compound 13 was isolated as a white foam: mp 130–133° C.; MS m/e 475 (MH+). Anal. calcd. for $C_{26}H_{30}N_6O_3$•3.6 HCl•3.9 $H_2O$•1.6 dioxane (798.05): C, 47.03; H, 6.82; N, 14.22. Found: C, 46.64; H, 7.02; N, 14.58.

EXAMPLE 16

β-[[[5,6,7,8-Tetrahydro-3-[2-(4-piperidinyl)E-ethylene]-1,2,4-triazolo[4,3-a]pyridin-8-yl]carbonyl] amino]-αS-benzylsulfonylamino-propanoic acid (14)

Compound 14 was prepared as described for compound 5 from intermediate AC3 (4.0 mmol) and methyl 3-amino-αS-benzylsulfonylaminopropanoate (3.0 mmol). Compound 14 was isolated as a glass: mp 125–128° C.; MS m/e 517 (MH+). Anal. calcd. for $C_{24}H_{32}N_6O_5S$•2.9 HCl•2.0 $H_2O$ (658.38): C, 43.78; H, 5.96; N, 12.76; Cl, 15.62. Found: C, 43.42; H, 6.12; N, 12.57; Cl, 15.37.

EXAMPLE 17

β-[[[5,6,7,8-Tetrahydro-3-[2-(4-piperidinyl)E-ethylene]-1,2,4-triazolo[4,3-a]pyridin-8-yl]carbonyl] amino]-αS-3-pyridylacetylamino-propanoic acid (15)

Compound 15 was prepared as described for compound 5 from intermediate AC3 (5.0 mmol) and methyl 3-amino-αS-3-pyridylacetylaminopropanoate (4.0 mmol). Compound 15 was isolated as white flakes: mp 128–131° C.; MS m/e 482 (MH+).

EXAMPLE 18

β-[[[5,6,7,8-Tetrahydro-3-[2-(4-piperidinyl)E-ethylene]-1,2,4-triazolo[4,3-a]pyridin-8-yl]carbonyl] amino]-αS-isobutyloxycarbonylamino-propanoic acid (16)

Compound 16 was prepared as described for compound 5 from intermediate AC3 (3.3 mmol) and methyl 3-amino-αS-isobutyloxycarbonylaminopropanoate (2.1 mmol). Compound 16 was isolated as white flakes: mp 130–133° C.; MS m/e 463 (MH+). Anal. calcd. for $C_{22}H_{34}N_6O_5$•2.2 HCl•2.0 $H_2O$•1.0 dioxane(666.90): C, 46.83; H, 7.28; N, 12.60; Cl, 11.70. Found: C, 47.21; H, 7.08; N, 12.27; Cl, 11.46.

EXAMPLE 19

β-[[[3-[2-(4-piperidinyl)ethyl]-1,2,4-triazolo[4,3-a] pyridin-8-yl]carbonyl]amino]-βS-3-pyridylpropanoic acid (17)

Compound 17 was prepared as described in Scheme AF. A dioxane (54 mL) solution of pyridine AF1 (2.0 g, 0.0108 mol) and hydrazine (0.40 mL, 1 eq) was heated at 60° C. for 2 h, cooled to rt, and evaporated to dryness. This product was treated with DCM (55 mL), AF2 (2.8 g, 1 eq), EDC hydrochloride (2.5 g, 1.2 eq), NMM (1.5 mL), and HOBT (2 mg), and stirred for 18 h at rt. This mixture was diluted with DCM (100 mL), and the organic layer washed with water (3×50 mL), dried (MgSO$_4$), and evaporated to a foam. The foam was treated with toluene (106 mL), 4 A molecular sieves, and acetic acid (6 mL), and heated in a Dean-Stark apparatus for 22 h. The reaction was cooled, evaporated, and the residue purified by silica gel chromatography (2% MeOH/DCM) to give AF3 (1.65 g) as a tan solid. Intermediate AF3 was carried forward to 17 as described in Scheme AA (see 1). Compound 17 was isolated as a white powder mp 117–120° C.; MS m/e 423 (MH+). Anal. calcd. for $C_{22}H_{26}N_6O_3$•3.0 HCl•2.0 $H_2O$ (567.89): C, 46.53; H. 5.86; N, 14.80; Cl, 18.73. Found: C, 46.59; H. 5.84; N, 14.51; Cl, 18.42.

EXAMPLE 20

As a specific embodiment of an oral composition, 100 mg of the compound 1 of Example 2 is formulated with sufficient finely divided lactose to provide a total amount of 580 to 590 mg to fill a size O hard gel capsule.

The triazolopyridine compounds of the present invention are GPIIb/IIIa antagonists. For instance, compound 1 exhibited 360 min duration in blocking canine ex vivo platelet aggregation when dosed at 3 mg/kg orally (see Table III). The compounds interrupt binding of fibrinogen to platelet glycoprotein IIb/IIIa (GPIIb/IIIa) and thereby inhibit platelet aggregation. Such compounds are, therefore, useful in treating platelet-mediated thrombotic disorders such as arterial and venous thrombosis, acute myocardial infarction, re-occlusion following thrombolytic therapy and angioplasty, and a variety of vaso-occlusive disorders. Because the final, common pathway in normal platelet aggregation is the binding of fibrinogen to activated, exposed GPIIb/IIIa, inhibition of this binding represents a plausible antithrombotic approach. The receptor is activated by stimuli such as ADP, collagen, and thrombin, exposing binding domains to two different peptide regions of fibrinogen: α-chain Arg-Gly-Asp (RGD) and γ-ychain 400–411. As demonstrated by the results of the pharmacological studies described hereinafter, the compounds of the present invention show the ability to block fibrinogen binding to isolated GPIIb/IIa ($IC_{50}$'s 0.0004–0.0072 $\mu$M), inhibit platelet aggregation in vitro in the presence of a various of platelet stimuli ($IC_{50}$'s 0.016–1.3 $\mu$M vs. thrombin), and furthermore, inhibit ex vivo platelet aggregation in animal models.

EXAMPLE 21

In Vito Solid Phase Purified Glycoprotein IIB/IIA Binding Assay

A 96 well Immulon-2 microtiter plate (Dynatech-Immulon) was coated with 50 $\mu$l/well of RGD-affinity purified GPIIb/IIIa (effective range 0.5–10 $\mu$g/mL) in 10 mM HEPES, 150 mM NaCl, 1 mM $MgCl_2$ at pH 7.4. The plate was covered and incubated overnight at 4° C. The GPIIb/IIa solution was discarded and 150 $\mu$l of 5% BSA was added and incubated at RT for 1–3 h. The plate was washed extensively with modified Tyrodes buffer. Biotinylated fibrinogen (25 $\mu$l/well) at 2×final concentration was added to the wells that contain the test compounds (25 $\mu$l/well). The plate was covered and incubated at RT for 2–4 h. Twenty minutes prior to incubation completion, one drop of Reagent A (Vecta Stain ABC Horse Radish Peroxidase kit, Vector Laboratories, Inc.) and one drop Reagent B were added with mixing to 5 mL modified Tyrodes buffer mix and let stand. The ligand solution was discarded and the plate washed (5×200 $\mu$l/well) with modified Tyrodes buffer. Vecta Stain HRP-Biotin-Avidin reagent (50 $\mu$l/well, as prepared above) was added and incubated at RT for 15 min. The Vecta Stain solution was discarded and the wells washed (5×200 $\mu$l/well) with modified Tyrodes buffer. Developing buffer (10 mL of 50 mM citrate/phosphate buffer @ pH 5.3, 6 mg o-phenylenediamine, 6 $\mu$l 30% $H_2O_2$; 50 $\mu$l/well) was added and incubated at RT for 3–5 min, and then 2N $H_2SO_4$ (50 $\mu$l/well) was added. The absorbance was read at 490 nM. The results are shown in Table II.

EXAMPLE 22

In Vitro Inhibition of Thrombin-Induced Gel-Filtered Platelet Aggression Assay

The percentage of platelet aggregation is calculated as an increase in light transmission of compound-treated platelet concentrate vs. control-treated platelet concentrate. Human blood was obtained from drug free, normal donors into tubes containing 0.1 3M sodium citrate. Platelet rich plasma (PRP) was collected by centrifugation of whole blood at 200×g for 10 min at 25° C. The PRP (5 mL) was gel filtered through Sepharose 2B (bed volume 50 mL), and the platelet count was adjusted to 2×10$^7$ platelets per sample. The following constituents were added to a siliconized cuvette: concentrated platelet filtrate and Tyrode's buffer (0.14M NaCl, 0.0027M KCl, 0.012M $NaHCO_3$, 0.76 mM $Na_2HPO_4$, 0.0055M glucose, 2 mg/mL BSA and 5.0 mM HEPES @ pH 7.4) in an amount equal to 350 $\mu$l, 50 $\mu$l of 20 mM calcium and 50 $\mu$l of the test compound. Aggregation was monitored in a BIODATA aggregometer for the 3 min following the addition of agonist (thrombin 50 $\mu$l of 1 unit/mL). The results are shown in Table II.

TABLE II

| | In Vitro Results | | | |
|---|---|---|---|---|
| | Fibrinogen Binding | | Platelet Aggregation* | |
| Cp # | % Inh. (50 $\mu$M) | $IC_{50}$ (nM) | % Inh. (50 $\mu$M) | $IC_{50}$ ($\mu$M) |
| 1 | 100% | 0.40 | 100% | 0.016 |
| 2 | 98% | 7.2 | 98% | 1.30 |
| 3 | 100% | 0.48 | 100% | 0.068 |
| 4 | 100% | 44.7 | 100% | 16.4 |
| 5 | 100% | 0.10 | 100% | 0.023 |
| 6 | 100% | 8.2 | 100% | 1.9 |
| 7 | 100% | 0.75 | 100% | 0.35 |
| 8 | 100% | 18.1 | 100% | 2.1 |
| 9 | 100% | 1.7 | 100% | 0.50 |
| 10 | 100% | 0.94 | 100% | 0.18 |
| 11 | 100% | 1.1 | 100% | 0.11 |
| 12 | 100% | 0.14 | 100% | 0.030 |
| 13 | 100% | 0.44 | 100% | 0.057 |
| 14 | 100% | 0.51 | 100% | 0.043 |
| 15 | 100% | 1.4 | 100% | 0.12 |
| 16 | 100% | 0.60 | 100% | 0.60 |
| 17 | 90% | 443 | NT | >1 |

*Thrombin-induced aggregation of gel-filtered platelets.

EXAMPLE 23

Ex Vivo Dog Study

Adult mongrel dogs (8–13 kg) were anesthetized with sodium pentobarbital (35 mg/kg, i.v.) and artificially respired. Arterial blood pressure and heart rate were measured using a Millar catheter-tip pressure transducer inserted in a femoral artery. Another Millar transducer was placed in the left ventricle (LV) via a carotid artery to measure LV end diastolic pressure and indices of myocardial contractility. A lead II electrocardiogram was recorded from limb electrodes. Catheters were placed in a femoral artery and vein to sample blood and infuse drugs, respectively. Responses were continuously monitored using a Modular Instruments data acquisition system.

Arterial blood samples (5–9 ml) were withdrawn into tubes containing 3.8% sodium citrate to prepare platelet rich plasma (PRP) and to determine effects on coagulation parameters: prothrombin time (PT) and activated partial thromboplastin time (APTT). Separate blood samples (1.5 ml) were withdrawn in EDTA to determine hematocrit and cell counts (platelets, RBC's and white cells). Template bleeding times were obtained from the buccal surface using a symplate incision devise and Whatman filter paper.

Aggregation of PRP was performed using a BioData aggregometer. Aggregation of whole blood used a Chronolog impedance aggregometer. PT and APTT were determined on either a BioData or ACL 3000+ coagulation analyzer. Cells were counted with a Sysmex K-1000.

Compounds were solubilized in a small volume of dimethylformamide (DMF) and diluted with saline to a final concentration of 10% DMF. Compounds were administered by the intravenous route with a Harvard infusion pump. Doses was administered over a 15 min interval at a constant rate of 0.33 ml/min. Data were obtained after each dose and in 30 min intervals following the end of drug administration. Oral doses were administered as aqueous solutions via syringe.

Compounds caused marked inhibition of ex vivo platelet aggregation responses. Thus, in whole blood, the compounds inhibited collagen-stimulated (or ADP) aggregation in doses of 0.1–10 mg/kg with marked inhibition of collagen stimulated platelet ATP release. In PRP, the compounds also inhibited collagen stimulated platelet aggregation with marked activity at 0.1–10 mg/kg. Compounds had no measurable hemodynamic effect in doses up to 1 mg/kg, iv. The drugs produce an increase in template bleeding time at 0.1–1 mg/kg with rapid recovery post treatment. No effects on coagulation (PT or APTT) were observed during treatment and platelet, white and RBC counts were unchanged at any dose of the compounds.

The results indicate that the compounds are broadly effective inhibitors of platelet aggregation ex vivo (antagonizing both collagen and ADP pathways) following iv administration of doses ranging from 0.3–1.0 mg/kg or 3 mg/kg orally. The antiaggregatory effects are accompanied by increases in bleeding time at the higher doses. No other hemodynamic or hematologic effects are observed. The results are shown in Table III.

TABLE III

Ex Vivo Dog Study Results

| | Intravenous Dosing | | Oral Dosing | |
|---|---|---|---|---|
| Cp # | Dose | Duration* | Dose | Duration* |
| 1 | 0.3 mpk | 180 min | 3 mpk | 360 min |
| 3 | 0.1 mpk | 120 min | 1 mpk | 300 min |
| 4 | NT | | 1 mpk | <30 min |
| 5 | 0.1 mpk | 120 min | 1 mpk | 360 min |
| 8 | NT | | 1 mpk | <30 min |
| 12 | 0.1 mpk | 150 min | 1 mpk | 360 min |

*Indicates duration of >50% inhibition of ADP-induced ex vivo platelet aggregation.
NT = not tested.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:
1. A compound of the formula selected from the group consisting of (I) and (II):

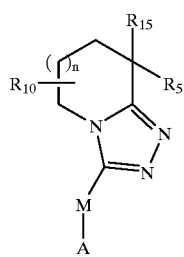

(I)

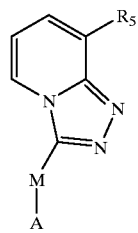

(II)

wherein M is $(CH_2)_m$, CH=CH, CH=CF, CF=CH, or C≡C;

n is an integer selected from the group consisting of 0, 1 and 2;

A is selected from the group consisting of piperidin-2-yl, piperidin-3-yl, piperidin-4-yl, piperazin-1-yl, pyrrolidin-2-yl, pyrrolidin-3-yl, $NHR_2$ and

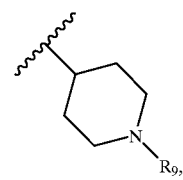

wherein R is selected from the group consisting of hydrogen, $C_1$–$C_8$ alkyl, CH=(NH), CMe=(NH), $C_2$–$C_6$ acyl, $C_1$–$C_8$ alkoxycarbonyl and ar($C_1$–$C_8$ alkoxy)carbonyl;

$R_2$ is selected from the group consisting of hydrogen, $C_1$–$C_8$ alkyl and $C_2$–$C_6$ acyl;

$R_{10}$ is selected from the group consisting of hydrogen and $C(O)N(R_1)YZ$, wherein $R_1$ is selected from the group consisting of hydrogen, $C_1$–$C_8$ alkyl and $C_3$–$C_8$ cycloalkyl;

Y is selected from the group consisting of $(CH_2)_p$, $CH(R_3)(CH_2)_q$, $(CH_2)_qCH(R_3)$, $(CH(CO_2R_4)CH_2)_q$, $(CH_2)_qCHOH$ and piperidine-3-carboxylic acid;

$R_3$ is selected from the group consisting of $C_1$–$C_8$ alkyl, $C_2$–$C_8$ alkenyl, $C_2$–$C_8$ alkynyl, aryl, ar($C_1$–$C_8$)alkyl and heteroaryl; p1 $R_4$ is selected from the group consisting of hydrogen, $C_1$–$C_8$ alkyl and $C_3$–$C_8$ cycloalkyl;

p is an integer selected from the group consisting of 2 and 3;

q is an integer selected from the group consisting of 1, 2, and 3;

Z is $CO_2R_8$;

$R_5$ is $C(O)NHQ(CHW)_rCO_2R_8$;

wherein Q is selected from the group consisting of $CH_2$, CH-aryl, CH-heteroaryl, CH-substituted-heteroaryl and CH-($C_1$–$C_8$)alkyl;

W is selected from the group consisting of hydrogen and $N(R_6)T$-$R_7$;

$R_6$ is selected from the group consisting of hydrogen, $C_1$–$C_8$ alkyl and $C_2$–$C_6$ acyl;

T is selected from the group consisting of C(O), C(N—CN) and $SO_2$;

$R_7$ is selected from the group consisting of $C_1$–$C_8$ alkyl, aryl, ar($C_1$–$C_8$)alkyl, ar($C_1$–$C_8$)alkoxy, $C_1$–$C_8$ alkoxy, ($C_1$–$C_8$)alkylamino, unsubstituted heteroaryl($C_0$–$C_8$) alkyl and substituted heteroaryl($C_0$–$C_8$)alkyl; and $R_8$ is hydrogen, $C_1$–$C_8$ alkyl, or $CH_2C(O)NR_{11}R_{12}$; wherein $R_{11}$ and $R_{12}$ are each independently selected from the group consisting of hydrogen, $C_1$–$C_8$ alkyl, and $C_3$–$C_8$ cycloalkyl;

m is an integer selected from the group consisting of 1, 2, and 3;

r is an integer selected from the group consisting of 0 and 1; and $R_{15}$ is selected from the group consisting of hydrogen and $C_1$–$C_8$ alkyl;

and pharmaceutically acceptable salts thereof.

2. The compound of claim 1, wherein:

wherein M is $(CH_2)_m$ or $CH=CH$;

$R_5$ is $C(O)NHQ(CHW)_rCO_2R_8$;

wherein Q is selected from the group consisting of $CH_2$, CH-heteroaryl and CH-substituted-heteroaryl;

W is selected from the group consisting of hydrogen and $N(R_6)T$-$R_7$; wherein $R_6$ is H; T is $C(O)$;

$R_7$ is selected from the group consisting of $C_1$–$C_8$ alkyl, aryl, ar($C_1$–$C_8$)alkyl, ar($C_1$–$C_8$)alkoxy, $C_1$–$C_8$ alkoxy, and ($C_1$–$C_8$)alkylamino;

$R_8$ is hydrogen, $C_1$–$C_8$ alkyl or $CH_2C(O)NR_{11}R_{12}$; wherein $R_{11}$ and $R_{12}$ are each independently $C_1$–$C_8$ alkyl;

$R_{10}$ is hydrogen;

$R_{15}$ is selected from the group consisting of hydrogen and $C_1$–$C_4$ alkyl; and r is 1;

or a pharmaceutically acceptable salts thereof.

3. The compound of claim 1 of the formula (I)

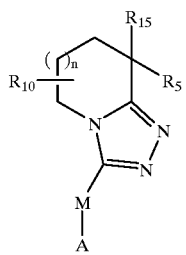

(I)

wherein M is selected from the group consisting of $(CH_2)_m$, $CH=CH$, and $C\equiv C$; and n is 1;

or a pharmaceutically acceptable salts thereof.

4. The compound of claim 3 selected from the group consisting of:

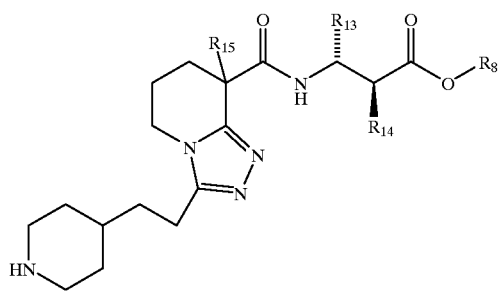

or

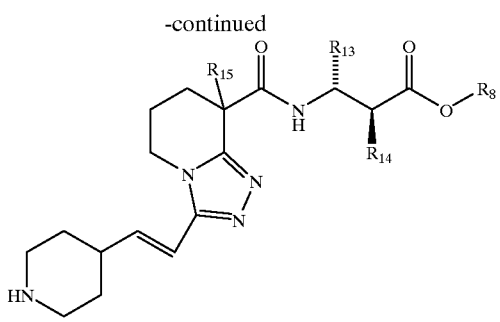

wherein $R_8$ is hydrogen or $CH_2CONEt_2$;

$R_{13}$ is selected from the group consisting of hydrogen, 3-pyridyl and 3-quinolinyl;

$R_{14}$ is selected from the group consisting of hydrogen and $NHCO_2CH_2Ph$; and $R_{15}$ is selected from the group consisting of hydrogen and methyl;

and pharmaceutically acceptable salts thereof.

5. The compound of claim 3 of the formula

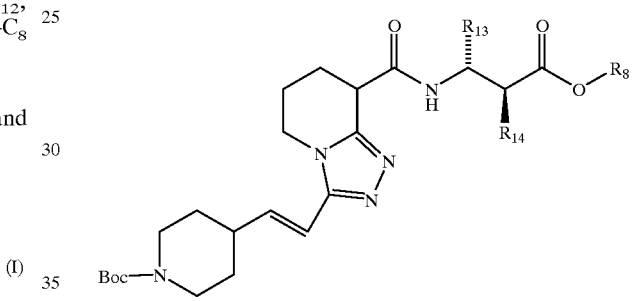

or a pharmaceutically acceptable salt thereof.

6. The compound of claim 1, selected from the group consisting of:

β-[[[5,6,7,8-Tetrahydro-3-[2-(4-piperidinyl)ethyl]-1,2,4-triazolo[4,3-a]pyridin-8-yl]carbonyl]amino]-βS-3-pyridinepropanoic acid;

β-[[[5,6,7,8-Tetrahydro-3-[2-(4-piperidinyl)ethyl]-1,2,4-triazolo[4,3-a]pyridin-8-yl]carbonyl]amino]-β-propanoic acid;

β-[[[5,6,7,8-Tetrahydro-3-[2-(4-piperidinyl)ethyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)ethyl]-1,2,4-triazolo[4,3-a]pyridin-8-yl]carbonyl]amino]-βS-3-pyridinepropanoic acid 2-(Diethylamino)-2-oxoethyl ester;

β-[[[5,6,7,8-Tetrahydro-3-[2-(4-piperidinyl)ethenyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)ethyl]-1,2,4-tiazolo[4,3-a]pyridin-8-yl]carbonyl]amino]-αS-benzyloxycarbonylamino-propanoic acid 2-(Diethylamino)-2-oxoethyl ester;

β-[[[5,6,7,8-Tetrahydro-3-[2-(4-piperidinyl)ethyl]-1,2,4-triazolo[4,3-a]pyridin-8-yl]carbonyl]amino]-β-3-thiophenepropanoic acid; or β-[[[5,6,7,8-Tetrahydro-8-methyl-3-[2-(4-piperidinyl)ethyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)Z-1-fluoroethenyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-β-4-pyridinepropanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-4-(3,5-dimethylisoxazolyl)sulfonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-βS-3-pyridylpropanoic acid;

β-[[[5,6,7,8-Tetrahydro-3-[2-(4-piperidinyl)E-ethenyl]-1,2,4-triazolo[4,3-a]pyridin-8-yl]carbonyl]amino]-βS-3-quinolinylpropanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-benzylsulfonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-3-pyridylacetylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-αS-isobutyloxycarbonylamino-propanoic acid;

β-[[[3-[2-(4-piperidinyl)ethyl]-1,2,4-triazolo[4,3-a]pyridin-8-yl]carbonyl]amino]-βS-3-pyridylpropanoic acid;

and pharmaceutically acceptable salts thereof.

7. The compound of claim 6, selected from the group consisting of:

β-[[[5,6,7,8-Tetrahydro-3-[2-(4-piperidinyl)E-ethenyl]-1,2,4-triazolo[4,3-a]pyridin-8-yl]carbonyl]amino]-αS-benzyloxycarbonylamino-propanoic acid;

β-[[[5,6,7,8-Tetrahydro-3-[2-(4-piperidinyl)E-ethenyl]-1,2,4-triazolo[4,3-a]pyridin-8-yl]carbonyl]amino]-βS-3-pyridylpropanoic acid;

and pharmaceutically acceptable salts thereof.

8. A pharmaceutical composition comprising a pharmaceutically acceptable carrier and a compound of claim 1.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

11. A method of treating a platelet-mediated thrombotic disorder in a subject in need thereof comprising administering to the subject a therapeutically effective amount of the compound of claim 1.

12. The method of claim 11, wherein the therapeutically effective amount of the compound is about 0.1 to about 300 mg/kg/day.

13. A method of treating a disorder mediated by GPIIb/IIIa in a subject in need thereof comprising administering to the subject a therapeutically effective amount of the compound of claim 1.

14. The method of claim 13, wherein the therapeutically effective amount of the compound is about 0.1 to about 300 mg/kg/day.

15. A method of treating a disorder mediated by GPIIb/IIIa in a subject in need thereof comprising administering to the subject a therapeutically effective amount of the composition of claim 9.

16. The method of claim 15, wherein the therapeutically effective amount of the compound is about 0.1 to about 300 mg/kg/day.

17. A method of inhibiting platelet aggregation in a subject in need thereof comprising administering to the subject a therapeutically effective amount of the compound of claim 1.

18. The method of claim 17, wherein the therapeutically effective amount of the compound is about 0.1 to about 300 mg/kg/day.

19. A compound of the formula AA3':

AA3' wherein M is selected from the group consisting of $(CH_2)_m$, CH=CH and C≡C;

A is selected from the group consisting of piperidin-2-yl, piperidin-3-yl, piperidin-4-yl, piperazin-1-yl, pyrrolidin-2-yl, pyrrolidin-3-yl, $NHR_2$ and wherein $R_9$ is selected from the group consisting of hydrogen, $C_1$–$C_8$ alkyl, CH=(NH), CMe=(NH), $C_2$–$C_6$ acyl, $C_1$–$C_8$ alkoxycarbonyl and ar($C_1$–$C_8$ alkoxy)carbonyl;

$R_2$ is selected from the group consisting of hydrogen, $C_1$–$C_8$ alkyl and $C_2$–$C_6$ acyl;

$R_{10}$ is selected from tie group consisting of hydrogen and $C(O)N(R_1)YZ$, wherein $R_1$ is selected from the group consisting of hydrogen, $C_1$–$C_8$ alkyl and $C_3$–$C_8$ cycloalkyl;

Y is selected from the group consisting of $(CH_2)_p$, $CH(R_3)(CH_2)_q$, $(CH_2)_qCH(R_3)$, $(CH(CO_2R_4)CH_2)_q$, $(CH_2)_q$CHOH and piperidine-3-carboxylic acid;

$R_3$ is selected from the group consisting of $C_1$–$C_8$ alkyl, $C_2$–$C_8$ alkenyl, $C_2$–$C_8$ alkynyl, aryl, ar($C_1$–$C_8$)alkyl and heteroaryl;

$R_4$ is selected from the group consisting of hydrogen, $C_1$–$C_8$ alkyl and $C_3$–$C_8$ cycloalkyl;

p is an integer selected from the group consisting of 2 and 3;

q is an integer selected from the group consisting of 1, 2, and 3;

Z is $CO_2R_8$;

$R_8$ is hydrogen, $C_1$–$C_8$ alkyl, or $CH_2C(O)NR_{11}R_{12}$; wherein $R_{11}$ and $R_{12}$ are each independently selected from the group consisting of hydrogen, $C_1$–$C_8$ alkyl, and $C_3$–$C_8$ cycloalkyl;

m is an integer selected from the roup consisting of 1, 2, and 3;

$R_{15}$ and $R_{16}$ are each independently selected from the group consisting of hydrogen and $C_1$–$C_8$ alkyl;

or a pharmaceutically acceptable salt and salts thereof.

20. The compound of claim 19 of the formula

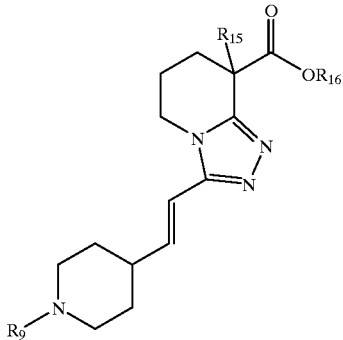

or a pharmaceutically acceptable salt thereof.

21. A compound selected from the group consisting of

AC4

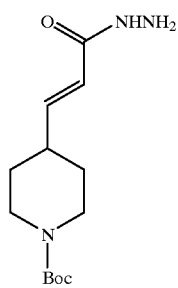

AC5

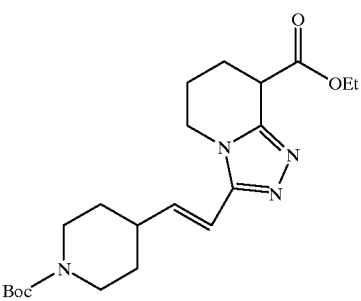

and pharmaceutically acceptable salts thereof.

22. A process for forming a compound of the formula (I) or a phanmaceutically acceptable salt thereof, (I)

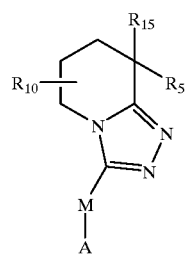

comprising reacting a compound of the formula AA3'

AA3'

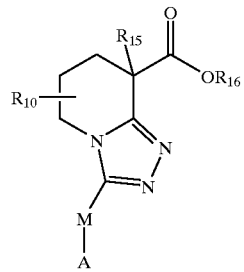

with a compound of the formula $H_2N$—$Q(CHW)CO_2R_8$ (AA4') to form the compound of the formula (I), wherein M is selected from the group consisting of $(CH_2)_m$, CH=CH and C≡C;

A is selected from the group consisting of piperidin-2-yl, piperidin-3-yl, piperidin-4-yl, piperazin-1-yl, pyrrolidin-2-yl, pyrrolidin-3-yl, $NHR_2$ and

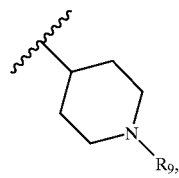

wherein $R_9$ is selected from the group consisting of hydrogen, $C_1$–$C_8$ alkyl, CH=(NH), CMe=(NH), $C_2$–$C_6$ acyl, $C_1$–$C_8$ alkoxycarbonyl and ar($C_1$–$C_8$ alkoxy)carbonyl;

$R_2$ is selected from the group consisting of hydrogen, $C_1$–$C_8$ alkyl and $C_2$–$C_6$ acyl;

$R_{10}$ is selected from the group consisting of hydrogen and $C(O)N(R_1)YZ$, wherein $R_1$ is selected from the group consisting of hydrogen, $C_1$–$C_8$ alkyl and $C_3$–$C_8$ cycloalkyl;

Y is selected from the group consisting of $(CH_2)_p$, $CH(R_3)(CH_2)_q$, $(CH_2)_qCH(R_3)$, $(CH(CO_2R_4)CH_2)_q$, $(CH_2)_q$ CHOH and piperidine-3-carboxylic acid;

$R_3$ is selected from the group consisting of $C_1$–$C_8$ alkyl, $C_2$–$C_8$ alkenyl, $C_2$–$C_8$ alkynyl, aryl, ar($C_1$–$C_8$)alkyl and heteroaryl;

$R_4$ is selected from the group consisting of hydrogen, $C_1$–$C_8$ alkyl and $C_3$–$C_8$ cycloalkyl;

p is an integer selected from the group consisting of 2 and 3;

q is an integer selected from the group consisting of 1, 2, and 3;

Z is $CO_2R_8$;

$R_5$ is $C(O)NHQ(CHW)CO_2R_8$;

wherein Q is selected from the group consisting of $CH_2$, CH-aryl, CH-heteroaryl, CH-substituted-heteroaryl and CH-($C_1$–$C_8$)alkyl;

W is selected from the group consisting of hydrogen and $N(R_6)T$-$R_7$;

$R_6$ is selected from the group consisting of hydrogen, $C_1$–$C_8$ alkyl and $C_2$–$C_6$ acyl;

T is selected from the group consisting of C(O), C(N—CN) and $SO_2$;

$R_7$ is selected from the group consisting of $C_1$–$C_8$ alkyl, aryl, ar($C_1$–$C_8$)alkyl, ar($C_1$–$C_8$)alkoxy, $C_1$–$C_8$ alkoxy, ($C_1$–$C_8$)alkylamino unsubstituted heteroaryl($C_0$–$C_8$) alkyl and substituted heteroaryl($C_0$–$C_8$)alkyl; and $R_8$ is hydrogen, $C_1$–$C_8$ alkyl, or $CH_2C(O)NR_{11}R_{12}$; wherein $R_{11}$ and $R_{12}$ are each independently selected the group consisting of from hydrogen, $C_1$–$C_8$ alkyl, and $C_3$–$C_8$ cycloalkyl;

m is an integer selected from the group consisting of 1, 2, and 3; and $R_{15}$ and R16 are each independently selected from the group consisting of hydrogen and $C_1$–$C_8$ alkyl.

23. The process of claim 22, further comprising dissolving a compound of formula AA2'

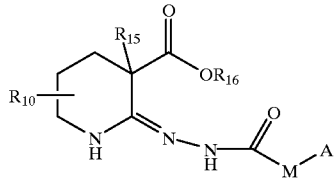

AA2' in a solvent selected from an alcohol or aromatic solvent to form a solution, and heating the solution to form the compound AA3'

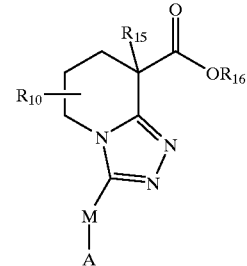

AA3'

* * * * *